United States Patent [19]

Modak et al.

[11] Patent Number: 5,567,495
[45] Date of Patent: Oct. 22, 1996

[54] INFECTION RESISTANT MEDICAL DEVICES

[75] Inventors: Shanta Modak, River Edge, N.J.; Lester Sampath, Nyack, N.Y.

[73] Assignee: The Trustees of Columbia University In The City of New York, New York, N.Y.

[21] Appl. No.: 273,329

[22] Filed: Jul. 11, 1994

Related U.S. Application Data

[63] Continuation-in-part of Ser. No. 103,087, Aug. 6, 1993, abandoned.

[51] Int. Cl.$^6$ .................................................. B29D 22/00
[52] U.S. Cl. .................. 428/36.9; 428/36.91; 428/36.92; 604/265
[58] Field of Search ................................ 428/36.9, 36.91, 428/36.92; 604/265

[56] References Cited

U.S. PATENT DOCUMENTS

| | | | |
|---|---|---|---|
| 3,566,874 | 3/1971 | Shepherd et al. | 128/349 |
| 4,432,766 | 2/1984 | Bellotti et al. | 604/283 |
| 4,612,337 | 9/1986 | Fox, Jr. et al. | 523/113 |
| 4,623,329 | 11/1986 | Drobish et al. | 604/29 |
| 4,723,950 | 2/1988 | Lee | 604/322 |
| 4,738,668 | 4/1988 | Bellotti et al. | 604/283 |
| 4,925,668 | 5/1990 | Khan et al. | 424/422 |
| 5,013,306 | 5/1991 | Solomon et al. | 604/265 |
| 5,013,717 | 5/1991 | Solomon et al. | 514/56 |
| 5,019,096 | 5/1991 | Fox, Jr. et al. | 623/1 |
| 5,061,254 | 10/1991 | Karakelle et al. | 604/265 |
| 5,061,738 | 10/1991 | Solomon et al. | 523/100 |
| 5,133,090 | 7/1992 | Modak et al. | 2/168 |
| 5,176,665 | 1/1993 | Watanabe et al. | 604/317 |
| 5,236,422 | 8/1993 | Eplett, Jr. | 604/265 |
| 5,263,930 | 11/1993 | Ensminger | 604/93 |

OTHER PUBLICATIONS

Segura et al., J. Clin. Micro., 27:2656–2659, 1989, "In Vitro Bacteriological Study of a New Hub Model for Intravascular Catheters and Infusion Equipment".

Messing et al., Clin. Nutrition, 9:220–225, 1990, "Antibiotic-Lock Technique is an Effective Treatment of Bacterial Catheter-Related Sepsis During Parenteral Nutrition".

*Primary Examiner*—James J. Seidleck
*Assistant Examiner*—Michael A. Williamson
*Attorney, Agent, or Firm*—Brumbaugh, Graves, Donohue & Raymond

[57] ABSTRACT

The present invention provides for medical devices which are antiinfective as a result of antiinfective agents impregnated onto their surfaces and/or antiinfective activity incorporated into their access sites. It is based, at least in part, on the discovery that certain combinations of antimicrobial agents and solvents change the surface characteristics of polymeric medical devices, thereby facilitating the retention of antimicrobial agents. It is further based on the discovery that the incorporation of antiinfective polymeric inserts into the access site of a medical device provides substantially improved antiinfective activity.

5 Claims, 1 Drawing Sheet

INFECTION RESISTANT MEDICAL DEVICES

SPECIFICATION

This application is a continuation-in-part of U.S. patent application Ser. No. 08/103,087, filed Aug. 6, 1993 by Modak and Sampath now abandoned.

INTRODUCTION

The present invention relates to medical devices which have been rendered infection resistant by impregnating their surfaces with antiinfective agents and/or by creating an antiinfective barrier at portals of entry for pathogens.

BACKGROUND OF THE INVENTION

The present invention is directed toward medical devices which minimize the risk of infection by inhibiting the entry, adherence, and/or proliferation of microbes.

Whenever a medical device comes in contact with a patient, a risk of infection is created. Thus, a contaminated examination glove, tongue depressor, or stethoscope could transmit infection. The risk of infection dramatically increases for invasive medical devices, such as intravenous catheters, arterial grafts, intrathecal or intracerebral shunts, which not only are, themselves, in intimate contact with body tissues and fluids, but also create a portal of entry for pathogens. A number of methods for reducing the risk of infection have been developed, none of which have been clinically proven to be completely satisfactory.

U.S. Pat. No. 3,566,874, issued Mar. 2, 1971, by Shepherd et al. discloses the coating of catheters, especially urinary catheters, with hydrophilic acrylate and methacrylate polymer, which are, themselves, said to be associated with antimicrobial activity. Shepherd et al. indicates that their antiinfective activity may be enhanced by incorporating antibiotic into the polymer coating. The soaking of polymer-coated catheters in aqueous solutions of antibiotics is disclosed.

U.S. Pat. No. 4,612,337, issued Sep. 16, 1986, by Fox, Jr. et al., teaches soaking a polymeric material with a solution of an antimicrobial agent dissolved in an organic solvent, soaking the polymeric material with an organic solvent for a metal salt, and resoaking the polymeric material with the solution of the antimicrobial in organic solvent. Acetic acid, chloroform, ethanol, acetone and ether are disclosed as suitable organic solvents.

U.S. Pat. No. 4,925,668, issued May 15, 1990, by Khan et al. discloses a substantially hydrophilic polymeric medical article having a coating of chlorhexidine and a silicone on its surface, and may have chlorhexidine bulk distributed throughout the article. Solutions of chlorhexidine and silicone oil in ethanol-Freon TF are disclosed.

U.S. Pat. No. 5,013,717, issued May 7, 1991, by Solomon et al. discloses medical articles coated with silicone and antithrombotic agent, using solvent systems such as toluene, petroleum ether, methylene chloride or fluorinated hydrocarbons, which may further comprise polar solvents such as ethanol or isopropanol.

U.S. Pat. No. 5,013,306, issued May 7, 1991, by Solomon et al., relates to polymeric medical articles steeped in a solution of chlorhexidine (preferably 5–15%) in water, methylene chloride or methanol.

U.S. Pat. No. 5,019,096, issued May 28, 1991, by Fox, Jr. et al., teaches the coating of medical articles with solutions of polymer and antiinfective agent to form a layer of polymer containing antiinfective agent on the surface of the article. Suitable solvents include acetic acid, methyl acetate, ethyl acetate, hexane, N-N-dimethylacetamide, tetrahydrofuran, alcohols, water, N-ethyl-2-pyrrolidone, n-cyclohexyl-2-pyrrolidone and mixtures thereof.

Certain devices have incorporated antiinfective agents in proximity to portals of entry.

U.S. Pat. No. 4,432,766, issued Feb. 21, 1984, and U.S. Pat. No. 4,738,668, issued Apr. 19, 1988, both by Bellotti et al., disclose a pair of separate conduits, each having an internal seal zone. The ends of the conduits may be joined, antiseptic (e.g. chlorine gas) may be instilled, and then the internal seals may be opened to permit fluid flow.

U.S. Pat. No. 4,623,329, issued Nov. 18, 1986, by Drobish et al., discloses a concentric, replenishable fluid antimicrobial agent reservoir about the shaft or drainage tube of a catheter.

Segura et al., 1989, J. Clin. Microbiol. 27: 2656–2659 discloses an intravascular catheter having a hub comprising an antiseptic chamber containing a solution of antiinfective agent, such as 3% iodinated alcohol.

Messing et al., 1990, Clinical Nutrition 9: 220–225 discloses the injection of antibiotic solution into an intravenous catheter, and retaining that solution for 12 hours per day, as a way of diminishing catheter-related sepsis in patients receiving parenteral nutrition.

U.S. Pat. No. 5,176,665, issued Jan. 5, 1993, by Watanabe et al. discloses a device which may be passed into a urine collecting container, and through which antiinfective agent may be introduced into the container. The device eliminates or prevents the proliferation of pathogens in the container.

U.S. Pat. No. 5,236,422, issued Aug. 17, 1993, by Eplett et al., discloses a cylindrical antiseptic cuff with an inner shaft to be placed along a urinary catheter within a patient's distal urethra. In alternative embodiments, the cuff may be charged with antimicrobial agent (e.g. antibiotic fluid), or may be constructed of concentric layers of material which may be successively removed once colonized with bacteria.

U.S. Pat. No. 5,263,930, issued Nov. 23, 1993, by Ensminger, discloses an implantable patient access port which provides a percutaneous route for access using an external filament such as an external catheter, needle, wire or optical fiber. The access port incorporates an internal reservoir for the retention of an antibacterial fluid and further includes a means for refilling the fluid chamber.

In contrast to the medical articles disclosed in the prior art, the present invention relates to an improved method of impregnating an article surface with antiinfective agent, and provides antiinfective activity in hubs and ports without the use of instilled fluids or gases.

SUMMARY OF THE INVENTION

The present invention provides for medical devices which are antiinfective as a result of antiinfective agents impregnated onto their surfaces and/or antiinfective activity incorporated into their access sites. It is based, at least in part, on the discovery that certain combinations of antimicrobial agents and solvents change the surface characteristics of polymeric medical devices, thereby facilitating the retention of antimicrobial agents. It is further based on the discovery that the incorporation of antiinfective polymeric inserts into the access site of a medical device provides substantially improved antiinfective activity.

3.1. ABBREVIATIONS

| | |
|---|---|
| $AgNO_3$ | silver nitrate |
| AgSD | silver sulfadiazine |
| CHA | chlorhexidine acetate |
| HBC | heparin benzalkonium chloride |
| LTSB | lecitin containing trypticase soy broth |
| THF | tetrahydrofuran |
| TSB | trypticase soy broth |

DETAILED DESCRIPTION OF THE INVENTION

Figure 1A:
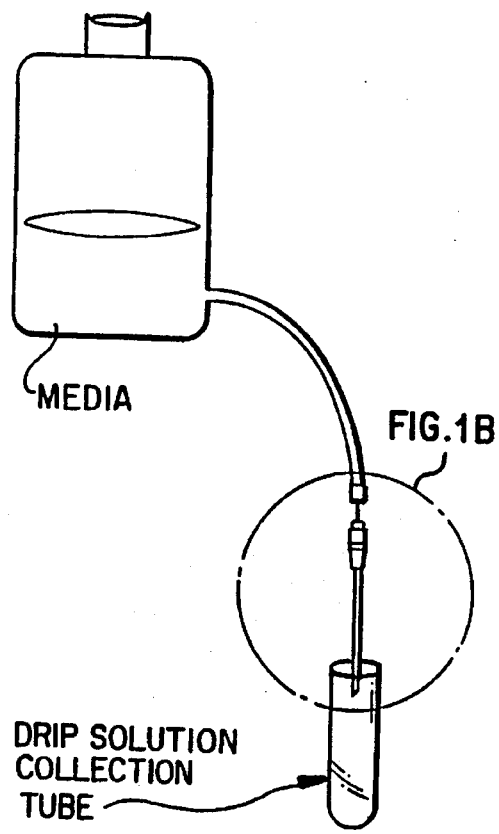
FIG. 1A shows the connection between a container of media and a drip solution collection tube.

For clarity of disclosure, and not by way of limitation, the detailed description of the invention is divided into the following subsections:

(a) impregnation of medical devices with antiinfective agent; and (b) antiinfective access sites.

IMPREGNATION OF MEDICAL DEVICES WITH ANTIINFECTIVE AGENT

The present invention provides for medical devices impregnated with antiinfective agent, as well as for methods of impregnating medical articles with antiinfective agent.

The present invention relates to a wide variety of medical devices, including devices fabricated from natural or synthetic polymers. For example, and not by way of limitation, the present invention relates to intravenous, intraarterial, intracerebral, intrathecal, and urinary catheters, arterial and venous grafts, stents, wound dressings, Omaya reservoirs, heart valves, artifical organs, prostheses, wound drainage bags, ostomy bags, urine collection bags, and containers for medical substances, such as blood storage bags, ampules and similar containers for injectable substances, etc.. In preferred embodiments, the present invention provides for catheters, especially intravenous catheters (e.g. central venous catheters). The term "catheter assembly", as used herein, refers to an apparatus comprising a catheter body, connected to an extension line by a hub, in which the extension line is further connected to an injection port by another hub. Alternatively, the catheter body may be connected, via a hub, directly to an injection port. In most conventional catheter assemblies, the hub and injection port have threaded ends which may be joined by screwing them together.

The medical devices may be fabricated, for example, and not by limitation, from natural and/or synthetic polymers, including hydrophilic as well as hydrophobic materials. Such materials include, but are not limited to, polyurethanes, nylon, Dacron, silicone, polytetrafluoroethylene and polyvinylchloride.

Antiinfective agents useful according to the invention include, but are not limited to, biguanides such as chlorhexidine and pharmaceutically acceptable salts thereof, antimicrobial metals, particularly silver and salts thereof (including silver nitrate ($AgNO_3$) and silver sulfadiazine (AgSD)), heparin, benzalkonium chloride, and antibiotics such as penicillins, cephalosporins, aminoglycosides, quinolones and glycopeptide antibiotics. combinations of agents may also be used.

According to particular embodiments of the invention, the surface of a medical device may be impregnated with antiinfective agent using a solution comprising antiinfective agent and one or more solvents which alter the surface characteristics of the device. This surface alteration is preferably minor, so as to improve impregnation of antiinfective agent without rendering the surface of the device rough or sticky. The composition of the solution may vary depending upon the physical characteristics of the device to be impregnated.

For example, but not by way of limitation, suitable solvent systems for polyurethane devices (such as polyurethane Triple Lumen catheters manufactured by Arrow International) include the following: (1) 20% THF/60% EtOH/ 20% $NH_4OH$, in which the antiinfective agent added may be, but is not limited to 1% CHA+0.2% AgSD (it is noted that in this and similar solvent systems, AgSD may preferably be solubilized first, prior to the addition of additional antiinfective agent); (2) 20% THF/80% EtOH, in which the antiinfective agent added may be, but is not limited to, 1% CHA +0.2% benzalkonium chloride; (3) 20% $NH_4OH$/80% EtOH, in which the antiinfective agent added may be, but is not limited to, 1% CHA+0.2% AgSD; (4) 100% EtOH, in which the antiinfective agent added may be, but is not limited to, 1% CHA+0.2% benzalkonium chloride; (5) 20% $NH_4OH$/40% EtOH/40% THF, in which the antiinfective agent added may be, but is not limited to, 5% CHA+0.5% AgSD or 1% CHA+0.5% AgSD; (6) 50% EtOH/50% $H_2O$, in which the antiinfective agent added may be, but is not limited to, 2–5% CHA; (7) 70% THF/30% EtOH, in which the antiinfective agent added may be, but is not limited to 1% CHA; (8) 60% THF/40% EtOH, in which the antiinfective agent added may be, but is not limited to, 1% CHA; (9) 50% THF/50% EtOH, in which the antiinfective agent added may be, but is not limited to, 1–5% CHA; (10) 40% THF/60% EtOH, in which the antiinfective agent added may be, but is not limited to, 1% CHA; (11) 30% THF/70% EtOH, in which the antiinfective agent added may be, but is not limited to, 1% CHA; (12) 20% THF/80% EtOH, in which the antiinfective agent added may be, but is not limited to, 1% CHA; (13) 40% THF/60% MeOH, in which the antiinfective agent added may be, but is not limited to, 0.5% CHA; (14) 20% $NH_4OH$/40% THF/40% MeOH, in which the antiinfective agent added may be, but is not limited to, 0.1% AgSD+0.5% CHA; (15) 40% THF/60% MeOH, in which the antiinfective agent added may be, but is not limited to, 0.1% benzalkonium chloride+0.5% CHA; (16) 2M ammonia in 20% MeOH/80% $H_2O$, in which the antiinfective agent added may be, but is not limited to, 2–5% CHA: (17) 20% $NH_4OH$/20% MeOH/60% $H_2O$, in which the antiinfective agent added may be, but is not limited to, 2–5% CHA+0.5% AgSD; (18) 10% $NH_4OH$/10% MeOH/ 80% THF, in which the antiinfective agent added may be, but is not limited to, 0.5% AgSD+1% CHA; (19) 5% MDX silicone in 90% THF/10% MeOH, in which the antiinfective agent added may be, but is not limited to, 3% CHA; (20) methylene chloride (up to 20%, and especially 10% in any miscible solvent); (21) dimethylacetamide (up to 20% and especially 10% in any miscible solvent); and (22) methylethyl-ketone (up to 60%). It should be noted that, as used herein, the specification of a solution which is, for example, X % solvent A/Y% solvent B/Z % solvent C, to which the antiinfective agent may be P % agent Q, where X+Y+Z= 100, indicates that concentration of agent Q is P % of the combined solution of A, B and C. Of the foregoing, the preferred solvent systems for altering the surface characteristics of articles fabricated from polyurethane are systems (10) and (21). In a preferred embodiment, a solution of 20% methylene chloride, 80% isopropanol, and 0.5–1% CHA and/or 0.5–1% Benzalkonium chloride is used.

For example, but not by way of limitation, suitable solvent systems for impregnation of silicone devices include the following: (1) 20% $NH_4OH$/20% MeOH/ 60% THF, in which the antiinfective agent added may be, but is not limited to, 5% CHA+1% AgSD; (2) 50% EtOH/50% THF, in which the antiinfective agent added may be, but is not limited to, 2–5% CHA; (3) 20% 2M ammonia in MeOH/ 80% THF, in which the antiinfective agent added may be, but is not limited to, 2–5% CHA; (4) 20% $NH_4OH$/20% MeOH/60% THF, in which the antiinfective agent added may be, but is not limited to, 2–5% CHA+0.5% AgSD; (5) 10% $NH_4OH$/10% MeOH/ 80% THF; (6) methylene chloride, to which antiinfective agent dissolved in a miscible solvent (e.g., isopropanol) is added; (7) dimethylacetamide, to which antiinfective agent dissolved in a miscible solvent (e.g., EtOH) is added; (8) methyl ethyl ketone, to which antiinfective agent dissolved in a miscible solvent (e.g., EtOH) is added; and (9) THF, to which antiinfective agent dissolved in a miscible solvent (e.g., EtOH) is added. Of the foregoing, the preferred solvent systems for altering the surface characteristics of articles fabricated from silicone are systems (6) and (9).

Antiinfective agent is preferably present in the soaking solution (i.e. a solvent system which alters the surface characteristics of the device) in relatively high concentrations so as to achieve rapid impregnation of high levels of agent into the device surface. For biguanides, suitable concentrations are 0.5% to 5%. For silver salts, such as silver sulfadiazine, silver carbonate, silver oxide and silver nitrate, suitable concentrations are 0.05 to 1.0%. In certain circumstances, where a patient may be sensitive to an antiinfective agent or where an interaction between the antiinfective agent impregnated into a device and a component of a solution to be stored in or passed through the device would be undesireable, the amount of antiinfective agent impregnated may be limited accordingly.

The medical device may then be soaked in the antiinfective agent-containing solution. If all surfaces of the device are to be impregnated, the device may be immersed in the solution. If only the interior of the device is to be impregnated, the device may be filled with the solution. If only the exterior of the device is to be coated, the access ports of the device (e.g. the ends of a catheter) may be sealed, and the body of the device washed or immersed with the solution. All of the foregoing methods are referred to, herein, as "soaking".

After soaking for a period of time sufficient to achieve the desired level of impregnation (generally 5 minutes to 24 hours), the device may be removed from contact with the solution and dried.

For surfaces which are refractory to impregnation, such as silicone, the surface may preferably be pre-treated prior to the use of impregnation methods discussed above. Pretreatment of the surface may be achieved using, for example, strong acids and bases, including, but not limited to, NaOH, KOH, $H_2PO_4$ (between 10–60% in aqueous solution). The silicone surface may be exposed to such agents for 5–30 minutes, washed, and dried, and then may be impregnated as set forth above.

If a polyurethane surface is refractory to impregnation, it may be pretreated by short-term exposure (e.g., a brief dip) to higher concentrations of organic solvents than those used for impregnation, or exposure to low concentrations (1–10%) of acids and alkali as set forth above.

In further embodiments of the invention, dual coatings of a medical device are provided. According to these embodiments, a solvent system which alters the surface characteristics of the device is used on one surface and a polymeric coating, which may comprise an antiinfective agent and/or antithrombotic agent (see below) may be used on the other surface. For example, and not by way of limitation, a solvent system as described above may be used to impregnate the internal surface of an device (e.g. the lumenal surface of a catheter) with antiinfective agent, and a polymeric coating may be applied to the external surface of the device (e.g. the external surface of a catheter). Suitable polymeric coatings include polyurethane, polylactic acid, polyethylene oxide, or silicone (including oils as well as cured silicone rubbers). The polymeric coating may be applied in a manner as set forth for possible means of impregnating the device. For example, and not by way of limitation, once the internal surface of the device is impregnated with antiinfective agent, the access site of the device may be closed and the polymeric coating applied to the exterior of the device. As a specific example, the lumenal surface of a catheter may be impregnated by filling the catheter with solution containing antiinfective agent, "soaking", then removing the solution and allowing the device to dry. Then, the ends of the catheter may be sealed (e.g. by heating, by the insertion of a rod which fills the lumen, or by blowing air through the device) and then the catheter may be dipped in a solution comprising polymer as well as antiinfective agent. Suitable coating methods are set forth in U.S. Pat. No. 5,133,090. For other specific, nonlimiting examples of catheters having dual coatings, see Sections 11, 13, 15 and 16, below.

In particular embodiments of the invention, bacterial adherence to the interior surface of a medical device, and, preferably, a catheter lumen may be prevented by impregnating the interior surface of the article with silver. The quantity of silver present may be insufficient to interact with medications, yet able to prevent adherence of bacteria to the impregnated surface. For example, and not by way of limitation, a polyurethane medical article such as a catheter may be soaked in a solution prepared by mixing equal portions of EtOH and a 10% solution of $AgNO_3$ in water. See Section 6, below. An impregnated device is considered to inhibit adherence of bacteria when adherence of bacteria is decreased by at least 50%.

Certain catheter materials appear to also affect polymorphonuclear phagocytosis. Some investigators have reported a correlation between catheter thrombogeneity and vulnerability to microbial colonization. Thrombus formation is promoted by host-derived matrix proteins such as fibronectin deposited on the catheter surface.

Coating the catheter surface with heparin has been previously shown by Kido, et al., 1982, Amer. J. Radiol. 139:957–961 to reduce thrombus formation during the early hours of insertion. Heparin is bonded to the catheter surface with benzalkonium chloride; a cationic, quaternary ammonium surfactant which has antiinfective properties.

Medical devices, such as catheters, prepared according to the invention, may further comprise coatings of heparin-benzalkonium chloride in order to improve anti-infective activity by inhibiting thrombus formation. For a specific, nonlimiting example, see Section 12, below.

ANTIINFECTIVE ACCESS SITES

Because access sites of medical devices, such as the hubs and injection ports of catheters and extension lines, have been shown to be a foremost source of bacterial colonization, development of infection-resistant access sites are warranted.

The term "access site", as used herein, refers to that portion of the device which serves as a boundary between the environment and the interior of the device. The environment is a potential source of pathogens. For example, the access sites of a catheter assembly are the hub and injection ports; the hub and injection ports are exposed to the environment external to the patient. Another access site of a catheter assembly is the catheter tip; it is exposed to the internal environment of the patient. Examples of other access sites associated with other medical devices include the portion of an ostomy bag which comes in contact with a patient stoma, the injection chamber of an Omaya reservoir (even though it is subcutaneous), and the soft polymeric seal of a container of injectable material through which a needle is passed in order to access the injectable material, to name but a few.

In some cases the antiinfective agents used to render an access site infection resistant may not, themselves, be suitable to coat the inner surface of the article itself. For example, the antiinfective agent may have a propensity to react with administered pharmaceuticals, or have toxic side effects. If used to coat the interior of the entire device, undesireable consequences may occur. However, such agents, comprised only in the relatively limited area of the access site(s), would be unlikely to me deleterious. Thus, more potent antiinfective agents may be incorporated into the access sites. This is advantageous, as pathogens must traverse the access site(s) in order to produce infection. By rendering the access site(s) antiinfective, a first line of defense against infection is created where it is most effective.

Suitable antiinfective agents include those set forth above (as well as increased concentrations of such agents), and also parachlorometaxylene (PCMX), Triclosan, and povidoneiodine. For example, and not by way of limitation, access sites may be dipped in solutions comprising 0.5–2% AgSD and 0.5–4% CHA.

According to the present invention, antiinfective activity can be created at an access site by (1) impregnating the access site with antiinfective agent and/or (2) incorporating an antiinfective insert into the access site.

The access site may be impregnated with antiinfective agent using solvent systems and methods as set forth in the preceding section. For example, and not by way of limitation, polyurethane catheter hubs and ports (e.g. as produced by Arrow, International) may be dipped into solutions of (1) 1% CHA/0.2% AgSD/20% THF/60% EtOH/20% $NH_4OH$; (2) 1% CHA/0.2% benzalkonium chloride/20% THF/ 80% EtOH; (3) 1% CHA/0.2% AgSD/20% $NH_4OH$/80% EtOH; (4) 1% CHA/0.2% benzalkonium chloride/100% EtOH; (5) 0.25% AgSD/1% CHA/50% $NH_4OH$/50% MeOH; (6) 0.25% AgSD/1% CHA/30% $NH_4OH$/50% MeOH/20% THF; or (7) 0.5% AgSD/1% CHA/30% $NH_4OH$/60% MeOH/10% THF. The external surfaces or internal surfaces of the access sites may be impregnateded exclusively, or both may be impregnated.

In further embodiments of the invention, an antiinfective disc, ring, seal or patch may be incorporated into the access site. Optionally, such disc, ring, seal or patch may be introduced either permanently or temporarily into the access site. If temporary, the antiinfective disc, ring, seal or patch may be exchanged while the device is in use.

For example, but not by way of limitation, an antiinfective disc or ring may be incorporated into the injection port or hub of a catheter assembly. If permanent, the disc or ring will remain intact throughout the use of the catheter or injection port. If temporary, the disc or ring may be changed, for example, each time the assembly is opened to the external environment.

Discs, rings, seals, or patches according to the invention may be fabricated, for example and not by way of limitation, from polyurethane, silicone, Dacron, Teflon, biodegradable polymers such as polylactic acid or polyglycolic acid, etc.

A disc may be fit into the access site, and may either serve as at least a partial barrier or, for example in the case of a catheter, may permit the flow of fluids through its substance. Alternatively, the disc may allow the passage of a needle.

A ring may function similarly to a disc, but would not serve a barrier function. It would provide for better transit of fluids.

A seal, as contemplated herein, would include a means for covering an access site. For example, but not by way of limitation, the soft polymer that allows passage of a needle into an injection port, and which is present on the exterior of the device, would be considered a seal.

A patch would include a flexible membrane which could be moved into position, on a catheter assembly, to cover the area where the catheter enters the skin of a patient. Similarly, a moveable antiinfective ring could be placed around the outside of a catheter (such as an intravenous catheter, urinary catheter, etc.) and moved into position and afixed at the point where the catheter passes into the body of the patient.

The antiinfective disc, ring, seal or patch may be impregnated with antiinfective agent using solvents systems and antiinfective agents as set forth above. In specific, non-limiting embodiments of the invention, a dacron or polyurethane ring may be dipped in one of the following solutions: (1) 1% CHA/0.2% AgSD/20% THF/60% EtOH/20% $NH_4OH$; (2) 1% CHA/0.2% Benzalkonium Chloride/20% THF/ 80% EtOH; (3) 1% CHA/0.2% AgSD/10% $NH_4OH$/ 80% EtOH; (4) 0.5% CHA/40% THF/60% MeOH or (5) 1% CHA/0.2% Benzalkonium Chloride/100% EtOH. For a specific, nonlimiting example of a Dacron disc prepared according to the invention, see Section 10, below.

A disc, ring, etc. may also be prepared, by specific, non-limiting, embodiments of the invention, by impregnating with antiinfective solution (as set forth above), such that the disc, ring, etc. retains fluid, so that upon connection with the hub, the fluid containing the antiinfective agent is expressed from the disc, ring, etc. and sterilizes the hub.

In one specific, non-limiting embodiment of the present invention, the luer-lock area of intravenous catheters may be rendered antiinfective. Solution containing various antiinfective agents, as set forth above, can be used for this purpose. The luer-lock area of the hub and the injection port may be dipped in the solutions and dried.

EXAMPLE: RENDERING CATHETER HUBS AND PORTS ANTIINFECTIVE BY DIPPING IN SELECT SOLVENTS CONTAINING ANTIINFECTIVE AGENT

MATERIALS AND METHODS

Catheter hubs and ports constructed of polyurethane (Arrow International, Inc.) were dipped in one of the following solutions:
(1) 1% CHA/0.2% AgSD/20% THF/60% EtOH/20% NH$_4$OH;
(2) 1% CHA/0.2% Benzalkonium Chloride/20% THF/80% EtOH;
(3) 1% CHA/0.2% AgSD/20% NH$_4$OH/80% EtOH; or
(4) 1% CHA/0.2% Benzalkonium Chloride/100% EtOH.

The hubs and ports were partially coated on both surfaces to an extent corresponding to area covered by the threads. These were air dried and stored.

RESULTS

The threaded areas of ten hubs and injection ports, treated as above, as well as untreated hubs and ports (control) were placed in 0.2 ml of *Staphylococcus aureus* culture (10$^4$ CFU/ml). After 24 hours, they were transferred to fresh culture. This procedure was repeated until the cultures showed presence of bacterial growth. Each day for seven days, growth in culture and adherence to the device were measured (0.1 ml of the culture was mixed with 0.1 ml of drug inactivating LTSB media and was subcultured on trypticase soy agar; adherence was tested as set forth in Section 6.2.1, below).

For untreated (control) hubs and ports, heavy growth in culture and heavy bacterial adherence were observed within twenty four hours.

For hubs and ports treated with any of the four solutions set forth above, there was no bacterial growth or adherence observed for four days. After five, six, and seven days, relatively light growth in culture, but no bacterial adherence, were observed.

EXAMPLE: PREPARATION OF ANTIINFECTIVE CATHETER ASSEMBLIES

MATERIALS AND METHODS

PREPARATION OF ANTIINFECTIVE DACRON AND POLYURETHANE RINGS FOR INSERTION INTO THE INJECTION PORT CAVITY

Dacron and polyurethane rings were prepared as follows: Dacron graft material manufactured by Meadox Inc. and trimmed to form rings (approximately 1 cm diameter, 1–2 cm length) and polyurethane rings prepared using 80A polyurethane pellets (Thermedics) were dipped for five seconds at room temperature in one of the following solutions:
(A) 1% CHA/0.5% AgSD/20% NH$_4$OH/80% EtOH;
(B) 1% CHA/0.5% Benzalkonium Chloride/100% EtOH;
(C) 1% AgSD in Ethanol;
(D) 1% AgSD/20% NH$_4$OH/80% EtOH;
(E) 1% AgSD/10% Phenoxyethanol/90% EtOH;
(F) 1% CHA/10% Phenoxyethanol/90% EtOH; or
(G) 1% AgSD/0.5% CHA/5% Phenoxyethanol/20% NH$_4$OH/75% EtOH and dried.

PREPARATION OF ANTIINFECTIVE HUBS AND PORTS

The methods and solutions set forth in Example Section 5, above, were used to prepare antiinfectives hubs and ports.

PREPARATION OF ANTIINFECTIVE CATHETERS

The interior surfaces of polyurethane Triple Lumen catheters (Arrow, Int'l.), polyurethane extension lines (Arrow, Int'l.), polyurethane hubs (Arrow, Int'l.) and polyurethane injection ports (Arrow, Int'l.) were rendered antiinfective by filling with a solution which is 50% EtOH and 50% (10% AgNO$_3$ in water), and therefore is 5% AgNO$_3$/50% EtOH/50% H$_2$O, removing the solution after four hours, and then allowing the articles to air dry.

RESULTS

LACK OF BACTERIAL ADHERENCE TO SURFACES IMPREGNATED WITH SILVER

The ability of bacteria to adhere to the luminal surfaces of extension lines impregnated with silver by filling with AgNO$_3$ solution, as set forth above, was tested as follows.

The inner surface of 6 cm segments of extension lines, which were either impregnated with silver or untreated (control), were exposed to a culture of *Staphylococcus aureus* (10$^4$ CFU/ml) by filling the segments and then incubating at 37 degrees Centigrade for 24 hours. The culture was then forced out into a culture tube and diluted 1:1 with drug inactivating media (LTSB), and subcultured.

After expelling the initial culture, the extension lines were refilled with fresh culture and the process repeated. After 24 hours, the culture was expelled, the catheters were flushed with media once, and then filled with media and vortexed to collect adherent organisms. The presence or absence of adherent organisms was determined by culturing. In each instance, for nine days, cultures obtained from control catheter segments tested positive for the presence of adherent bacteria, whereas cultures of silver-impregnated catheter segments were negative.

ANTIINFECTIVE CATHETER ASSEMBLIES

An in vitro model of a continuous flow system (See FIG. 1) was used to test the antiinfective activity of catheter assemblies comprising hubs, ports, discs, and extension lines as set forth above. Twice a day, in the morning and in the evening, the hub and port were infected with 10$^6$ CFU *S. aureus*. After ten days of continuous flow the bacterial adherence on the hub, injection port and extension lines was determined.

Untreated assemblies were found to yield greater than 10$^6$ CFU associated with the hub and port and greater than 10$^7$ CFU associated with the extension line.

For an assembly consisting of (1) a hub and port dipped in 1% CHA/0.2% AgSD/10% NH$_4$OH/80% EtOH and (2) an untreated extension line, although no bacterial growth was observed from the hub and port, the extension line yielded 1.8×10$^3$ CFU. This growth could be reduced to zero by incorporating an antimicrobial Dacron disc, dipped in 1% CHA/0.5% AgSD/20% NH$_4$OH/80% EtOH, into the injection port of the assembly. Alternatively, growth could be reduced to zero by impregnating the luminal surface of the extension line with silver.

Similarly, an assembly consisting of (1) a hub and port dipped in 1% CHA/0.2% Benzalkonium Chloride/100% EtOH and (2) an untreated extension line, although no bacterial growth was observed from the hub and port, the extension line yielded $1.5\times10^3$ CFU. This growth was reduced to zero in an assembly further containing an antimicrobial Dacron disc, dipped in 1% CHA/0.5% Benzalkonium Chloride/100% EtOH in the injection port. Growth was also reduced to zero in an assembly which did not contain a disc, but in which the luminal surface of the extension line was impregnated with silver.

The foregoing results demonstrate the advantages of incorporating an antiinfective disc and/or of impregnating the luminal surface with silver.

EXAMPLE: ANTIINFECTIVE ACTIVITY OF POLYMERS SOAKED IN TETRAHYDROFURAN CONTAINING SOLVENT SYSTEMS

MATERIALS AND METHODS

IMPREGNATION OF HYDROPHOBIC SUBSTRATE

Silicone central venous catheters (Davol, Inc.) were soaked in 5% CHA/1% AgSD/20% NH$_4$OH/20% MeOH/60% THF (the AgSD dissolved in the solvent system prior to the addition of CHA) for 15 minutes such that both internal and external surfaces were impregnated with CHA and AgSD. The catheter was then removed and dried at room temperature for two hours.

IMPREGNATION OF HYDROPHILIC SUBSTRATE

Polyurethane catheters (Triple Lumen, Arrow, Int'l.) hubs, and injection ports were soaked, for two hours, in either (1) 5% CHA/0.5% AgSD dissolved in a solvent system consisting of 20% NH$_4$OH/40% EtOH/40% THF; or (2) 5% CHA/50% EtOH/50% H$_2$O. The catheters and ports were then dried at room temperature for two hours.

RESULTS

In order to evaluate the antiinfective activity of the catheters, hubs and ports prepared as set forth above, the zones of inhibition associated with each article were determined as follows.

Either a 1 cm catheter segment, a hub or a port, prepared as described, were placed in trypicase soy agar plates inoculated with $10^5$ CFU of *S. aureus* and incubated at 37 degrees Centigrade for 24 hours. The zone of inhibition was then measured, and the articles were transferred to fresh culture plates on a daily basis, until no zone of inhibition was detectable. The results are set forth in Table A.

TABLE A

| | Zones of Inhibition (mm) | | | | |
|---|---|---|---|---|---|
| | Silicone catheter | Polyureth. catheter | | Polyureth. Hub | Polyureth. Port |
| Days | AgSD + CHA | AgSD + CHA | CHA | AgSD + CHA | AgSD + CHA |
| 1 | 16 | 18 | 16 | 15 | 21 |
| 2 | 14 | 15 | 14 | 0 | 10 |
| 3 | 13 | 13 | 13 | | |
| 4 | 12 | 10 | 12 | | |
| 5 | 10 | 10 | 10 | | |
| 6 | 10 | 10 | 10 | | |
| 7 | 9 | 9 | 9 | | |

The foregoing results demonstrate that the catheters impregnated with antiinfective agents, as set forth above, demonstrated antibacterial activity.

EXAMPLE: IMPREGNATION WITH ANTIINFECTIVE AGENT USING SOLVENTS THAT ALTER THE ARTICLE SURFACE

Polyurethane catheter (Triple Lumen, Arrow, Int'l.) segments were dipped in the following solutions of CHA, rinsed, and then evaluated for surface changes and for antibacterial activity using zone of inhibition studies. The results are set forth in Table B.

TABLE B

| | Surface | Days Antibacterial Activity |
|---|---|---|
| 1) 1% CHA/70% THF/30% EtOH | damaged | >8 |
| 2) 1% CHA/60% THF/40% EtOH | damaged | >8 |
| 3) 1% CHA/50% THF/50% EtOH | slightly altered | 6 |
| 4) 1% CHA/40% THF/60% EtOH | slightly altered | 6 |
| 5) 1% CHA/30% THF/70% EtOH | slightly altered | 2 |
| 6) 1% CHA/20% THF/80% EtOH | slightly altered | 2 |

The best solvent system appears to be 1% CHA/40% THF/60% EtOH. This solvent system was used to impregnate a catheter assembly in Section 10, below.

EXAMPLE: IMPREGNATION OF CATHETER ASSEMBLIES USING SURFACE-ALTERING SOLVENT SYSTEMS

MATERIALS AND METHODS

Polyurethane catheters, extension lines, hubs, and injection ports (Arrow Int'l.) were dipped in the following solutions, then dried at room temperature for one hour.

Solution A: 0.5% CHA/40% THF/60% MeOH

Solution B: 0.1% AgSD/0.5% CHA/20% NH$_4$OH/ 40% THF/40% MeOH

Solution C: 0.1% Benzalkonium chloride/0.5% CHA/ 60% MeOH/40% THF

RESULTS

To test the antiinfective activities of articles prepared in the foregoing manner, 10 microliters of *S. aureus* culture ($10^8$ CFU/ml) were spread on the threads of the injection port and hub. These two parts were then screwed together, and incubated for 6 hours at room temperature. Articles which had not been dipped in antiinfective solutions were used as controls, and inoculated the same way. Following incubation, 5 ml TSB was passed through the system, collected, and then cultured for 24 hours to determine whether any live bacteria from the hub or port had escaped into the fluid passing through the system. The results are presented in Table C. Growth was quantitated by measuring turbidity.

TABLE C

| Solution Used | Growth in Culture (Days) | | | | | | | | |
| --- | --- | --- | --- | --- | --- | --- | --- | --- | --- |
| For Dipping | 1 | 2 | 3 | 4 | 5 | 6 | 7 | 8 | 9 |
| None (Control) | + | + | + | + | + | + | + | + | + |
| A | − | − | − | + | + | + | + | + | + |
| B | − | − | − | − | − | + | + | + | + |
| C | − | − | − | − | + | + | + | + | + |

EXAMPLE: PREPARATION OF CATHETER ASSEMBLY HAVING ANTIINFECTIVE DACRON SPONGE IN PORT

MATERIALS AND METHODS

PREPARATION OF CATHETER BODY AND PORTS

Polyurethane extension lines, catheter bodies, hubs and injection ports were soaked in a solution containing 1% CHA/0.5% AgSD/20% $NH_4OH$/40% THF/60% Ethanol (Solution A) such that internal and external surfaces were impregnated with CHA and AgSD. After drying, the ends of the catheter body were sealed and the catheter was dipped into a solution containing 3% polyurethane/1.5% CHA/ 0.75% AgSD (Solution B).

IMPREGNATION OF SPONGE DISKS

Dacron fabric in the shape of a tube (1 cm diameter) was first dipped in solution A. After drying it was dipped into solution B and then dried. The Dacron sponge cuff (2 mm length) was inserted in the injection port.

RESULTS

Figure 1B:
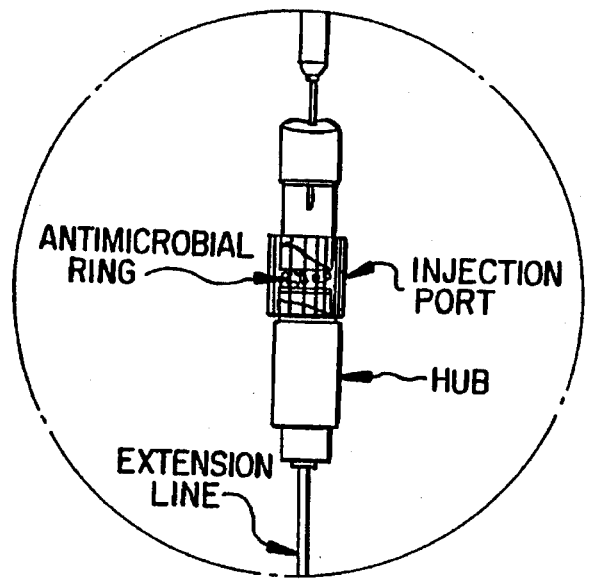
FIG. 1B shows an enlarged view of the injection port connecting the structures of FIG. 1A.

The effects of impregnating the hub, injection port and extension line with AgSD+CHA on luminal bacterial adherence were evaluated as follows. A continuous flow of fluid through the injection port, hub and extension line was maintained using a system as depicted in FIG. 1.

The grooved portions of the hub and injection port (which screw together) were infected twice a day with 10 microliters of *S. aureus* culture ($10^8$ CFU/ml). Eight liters of 50% normal saline+50% sterile trypticase soy broth ("TSB") was passed through the above system at a drip rate of 50–75 drops/minute for 4 days. Each day the broth was allowed to drip through the system for 8 hours and then stopped for 16 hours. The experiment was then terminated and the extension line, hub and injection port were disconnected.

The outer surface of the unit was sterilized by wiping with 70% ethanol and the end of the extension line (about 2 cm) was cut out. The unit was then flushed with 2 ml TSB through the injection port, hub, and extension line and the TSB was collected and a 0.2 ml aliquot was subcultured for determining the bacterial counts in the fluid. The hubs and the injection ports were disconnected and the bacterial adherence on the hubs and injection ports was determined by rolling them on trypticase agar plates.

The bacterial adherence onto specific portions of the extension line was determined as follows. After wiping the outer surface with 70% EtOH, the extension line was cut into 2 segments, one proximal to the hub and a second distal to the hub. Each segment was placed in 5 ml TSB and vortexed at low speed for 2 minutes. The segments were then removed and placed in 5 ml drug inactivating media (LTSB) and vortexed at high speed for 2 minutes to detach all the adherent bacteria.

One control group (untreated catheter assemblies) and two test groups were used in the study. The two test groups were catheter assemblies prepared by either (1) dipping into a solution of 1% CHA/0.5% AgSD/20% $NH_4OH$/ 40% THF/60% Ethanol or (2) dipping in the same solution, and also containing a dacron sponge (impregnated with AgSD+ CHA as described earlier) inside the injection port.

The results of the study are given in the Table D below.

TABLE D

| | Colony Counts* (CFU) | | |
| --- | --- | --- | --- |
| Group | Control | Test Group 1 | Test Group 2 |
| Fluid flushed through the unit | >$10^5$ | $10^4$ | 0 |
| Hub | >$10^5$ | 0 | 0 |
| Injection Port | >$10^5$ | 3+ | 0 |
| Extension Line-Lumen (Proximal) | $7 \times 10^4$ | 0 | 0 |
| Extension Line-Lumen (Distal) | $6.8 \times 10^4$ | 0 | 0 |

*CFU counts given above are as follows: for hub and port the numbers represent CFU/hub or port; for extension lines and catheters the results are given as CFU/cm segment.

These data indicate that the use of impregnated hubs, injection ports and lumens of extension lines and catheters prevents bacterial adherence to both luminal and external surfaces.

EXAMPLE: CATHETERS HAVING DIFFERENT ANTIINFECTIVE AGENTS ON EXTERNAL AND INTERNAL SURFACES

MATERIALS AND METHODS

FIRST PREPARATIVE METHOD

Polyurethane catheter segments (Arrow International, Triple Lumen) were soaked for 24 hours in a solution containing 2% or 5% chlorhexidine acetate in 50% reagent alcohol/50% water such that both internal and external surfaces were impregnated. The catheter segments were then dried at 70° C. for 30 minutes and then washed with water in a vortex mixer for 5 seconds. After drying at 20°–30° C. for 30 minutes, both ends of the catheter segment were sealed by heat.

The sealed catheter segments were dipped into a solution of 3% polyurethane (Tecoflex®-93A, Termedics, Inc.), 1.5% chlorhexidine acetate and 0.75% silver sulfadiazine in 70% THF/30% reagent alcohol to form a coating on the exterior of the catheter segments. The catheter segments were then dried at 70° C. for 30 minutes and for 24 hours at room temperature.

SECOND PREPARATIVE METHOD

The First Preparative Method was repeated, except that 20% 2M ammonia in methanol and 80% water was used as a solvent in place of the 50/50 alcohol/water mixture.

THIRD PREPARATIVE METHOD

The Second Preparative Method was repeated, except that the solution contained 0.5% lactic acid and 0.5% mandelic acid which have been found to be effective in preventing bacterial adherence to the urinary tract.

FOURTH PREPARATIVE METHOD

The First Preparative Method was repeated except that the soaking solution used was 2% or 5% chlorhexidine acetate and 0.5% silver sulfadiazine in 20% ammonia, 20% methanol and 60% water.

FIFTH PREPARATIVE METHOD

The First, Second, Third and Fourth Preparative Methods were applied to silicone catheter segments by replacing the water component in the soaking solution with THF.

RESULTS

To test the antiinfective properties of polyurethane catheter segments made in accordance with the invention, 2 cm long pieces of the treated catheter segments, open on both ends, were soaked in trypticase soy broth (4 ml/segment) at 37° C. to simulate exposure to body fluids. Three segments of each type were removed periodically and tested for bacterial adherence.

To test for adherence, the pieces of treated catheter were suspended in 2 ml of trypticase soy broth containing $10^7$ CFU of *Staphylococcus epidermidis* and incubated in a water-bath shaker at 37° C. for 4 hours. Untreated control catheter pieces and pieces subjected only to soaking or exterior coating were treated in parallel.

At the end of the 4 hour incubation, the catheter pieces were removed, blotted dry, vortexed in sterile TSB at low speed for 5 seconds, blotted dry again, and rolled over a trypticase soy agar plate. This results in the transfer of microorganisms to the plate if adherence to the outer surface has occurred.

The catheter pieces were then placed in 2 ml of lecithin containing trypticase soy broth (LTSB), which inactivates chlorhexidine, and vortexed at high speed for 15 seconds. The catheter pieces were removed and processed by the roll/plate technique described above. In addition, a 0.2 ml aliquot of the LTSB was subcultured on a trypticase soy agar plate.

All of the plates were incubated at 37° C. for 24 hours and the number of colonies were counted. The total number of colonies counted from all three platings were combined as a measure of resistance to infection. The results are summarized in Table E.

TABLE E

| Inner Anti-infective | Outer Coating | Treatment Method | Soaking Time In Presence of *Staph. epidermidis* | | |
|---|---|---|---|---|---|
| | | | 0 | 1 day | 4 days |
| 2% CHA | 3% PU 1.5% CHA 0.75% AgSD | Ex. 1 | 0 | 1 | 85 |
| 2% CHA 0.5% lactic acid 0.5% mandelic acid | 3% PU 1.5% CHA 0.75% AgSD | Ex. 3 | 0 | 0 | 25 |
| 2% CHA 0.5% AgSD | 3% PU 1.5% CHA 0.75% AgSD | Ex. 4 | 0 | 0 | 30 |
| Controls | | | | | |
| 0 | 0 | untreated | 100 | 200 | 1,000 |
| 2% CHA | 0 | Ex. 1 | 0 | 0 | 750 |
| 0 | 3% PU 1.5% CHA 0.75% AgSD | Ex. 1 | 0 | 0 | 150 |

Additional catheter pieces were tested using the above protocol, except that the bacterial culture used contained $4\times10^7$ CFU. The results are summarized in Table F.

TABLE F

| Inner Anti-infective | Outer Coating | Treatment Method | Soaking Time In Presence of *Staph. epidermidis* | | |
|---|---|---|---|---|---|
| | | | 0 | 1 day | 5 days |
| 5% CHA | 3% PU 1.5% CHA 0.75% AgSD | Ex. 1 | 0 | 0 | 0 |
| 5% CHA 0.5% AgSD | 3% PU 1.5% CHA 0.75% AgSD | Ex. 4 | 0 | 0 | 0 |
| Controls | | | | | |
| 0 | 0 | | 100 | 1,000 | 10,000 |
| 0 | 3% PU 1.5% CHA 0.75% AgSD | | 0 | 0 | 1,000 |

In further experiments, eight 2 cm pieces of catheters, prepared in accordance with the First, Third and Fourth Preparative Methods, were suspended in 12 ml of TSB inoculated with $10^6$ CFU *Staphylococcus epidermidis* and incubated in a water-bath shaker at 37° C. Two pieces of each type were removed at intervals and tested for bacterial adherence as described above. The remaining pieces were transferred to fresh TSB incubated with $10^6$ CFU of *Staphylococcus epidermidis* and inoculated.

The results, shown in Table G, together with those shown in Tables E and F, demonstrate the surprising effectiveness of using both a soaking treatment and an outer coating to impart antiinfective properties to the lumenal and outer surfaces of the catheter, respectively.

TABLE G

| Inner Anti-infective | Outer Coating | Treatment Method | Exposure Time to: | |
|---|---|---|---|---|
| | | | 24 hours | 48 hours |
| 2% CHA | 3% PU 1.5% CHA 0.75% AgSD | Ex. 1 | 0 | 83 |
| 2% CHA 0.5% lactic acid | 3% PU 1.5% CHA 0.75% AgSD | Ex. 3 | 0 | 63 |

TABLE G-continued

| Inner Anti-infective | Outer Coating | Treatment Method | Exposure Time to: 24 hours | 48 hours |
|---|---|---|---|---|
| 0.5% mandelic acid 2% CHA 0.5% AgSD | 3% PU 1.5% CHA 0.75% AgSD | Ex. 4 | 0 | 15 |
| Controls | | | | |
| 0 | 0 | | 5,000 | 10,000 |
| 0 | 3% PU 1.5% CHA 0.75% AgSD | | 0 | 328 |

This is significant because the attachment of bacteria to the surface of medical articles has been recognized as an important initial step in the pathogenesis of foreign body infection. The bacterial production of extracellular glycocalyx, a polysaccharide-containing component outside the cell wall (slime), facilitates their adhesion to the article. The fibrous glycocalyx extends from the bacterial cell surface and surrounds individual cells or colonies, protecting them from phagocytes and biocides while providing a suitable environment for the transport of nutrients. Once formed, the bacterial biofilm continues to be a source for the spread of infection to other parts of the body by bacterial detachment and biofilm sloughing.

A well known example of this problem was the mortality due to massive infections in patients receiving artificial hearts (Jarvik hearts). Similar situations are encountered in cystic fibrosis patients, where biofilm formation by *Pseudomonas aeruginosa* prevents the effective control of the disease by antibiotics.

EXAMPLE: CATHETERS OF DECREASED THROMBOGENICITY

Catheter segments were treated in accordance with the invention by soaking pieces of polyurethane catheters in a solution of heparin-benzalkonium chloride (HBC) complex (1.6% HBC in isopropanol) for two hours at 20–°30° C. The soaked pieces were then dried and the ends sealed by heating.

The exterior of the sealed catheter pieces were then coated with 3% polyurethane, 1.5% chlorhexidine acetate and 0.75% silver sulfadiazine in 75% THF/25% ethanol. The resulting coated pieces were then unsealed and tested for bacterial adherence as described in Section 11.2, above.

A second set of samples was prepared by this same method except that after the HBC treatment and before sealing, the catheter pieces were soaked in 5% chlorhexidine in 50% water/50% ethanol for 2 hours at 20°–30° C. These pieces were also tested for adherence.

The results, shown in Table H, illustrate the clear superiority of the invention for providing effective control of bacterial adherence.

TABLE H

| Inner Anti-infective | Outer Coating | Soaking Time In Presence of *Staph. epidermidis* | | | |
|---|---|---|---|---|---|
| | | 0 | 1 day | 3 days | 5 days |
| HBC | 3% PU 1.5% CHA 0.75% AgSD | 0 | 0 | 7 | 370 |
| HBC/CHA | 3% PU 1.5% CHA 0.75% AgSD | 0 | 0 | 10 | 1,086 |
| Controls | | | | | |
| 0 | 0 | 100 | n.d. | 1,000 | >50,000 |
| 0 | 3% PU 1.5% CHA 0.75% AgSD | 0 | 0 | 2 | 26,849 |
| HBC | 0 | 0 | 0 | 390 | 29,008 |

EXAMPLE: COATED SILICONE CATHETERS

Silicone catheter segments were coated inside and out using two variations of the method of the invention. In the first variation, the pieces were soaked in 0.5% AgSD and 1% CHA in 10% ammonia, 10% methanol and 80% THF for 24 hours at 20°–30° C. After drying for 30 minutes, the outer surfaces were wiped with THF to remove excess antiinfective agent and the ends were sealed. The pieces were then dipped in a solution containing 5% MDX silicone (MDX 4-4210, Dow Corning) and 3% CHA in 90% THF/10% methanol and removed immediately. After drying for 5 minutes at 100° C. they were dipped into 5% Silastic A silicone in hexane and then dried for 30 minutes at 100° C. and 24 hours at room temperature.

In the second variation, the silicone catheter pieces were soaked in 1.6% HBC in isopropanol for 1 hour at 20–°30° C., dried and wiped on the outer surface and then sealed on the ends. The outer coating was then applied in the same manner.

The samples prepared were then tested for bacterial adherence using the technique described in Section 11.2. The results are shown in Table I.

TABLE I

| Inner Anti-infective | Outer Coating | Soaking Time In Presence of *Staph. epidermidis* | | |
|---|---|---|---|---|
| | | 0 | 1 day | 4 days |
| 1% CHA 0.5% AgSD | Silicone/CHA | 0 | 0 | 1,010 |
| HBC | Silicone/CHA | 0 | 0 | 10 |
| Controls | | | | |
| 0 | Silicone/CHA | 0 | 0 | 9,466 |
| 0 | 0 | 1,000 | >1,000 | >10,000 |

EXAMPLE: IMPREGNATED HUBS AND PORTS

Impregnation of catheter hubs and ports with an antiinfective agent was carried out as follows. Hubs and ports made from polyurethane (Arrow International) were treated with antiinfective agents by soaking using three alternative procedures.

In the first procedure, AgSD was dissolved in 14.8M ammonia. Chlorhexidine acetate was dissolved in methanol. The two solutions were then combined to form a soaking solution containing 0.25% AgSD and 1% CHA in 50% ammonia/50% methanol. The hubs and ports were dipped in this solution and removed immediately at 20–°30° C. and then dried at 70° C. for 30 minutes.

In the second and third procedures, THF was added to the combined solutions to yield final compositions of 0.25% AgSD, 1% CHA in 30% ammonia/50% methanol and 20% THF or 0.5% AgSD and 1% CHA in 30% ammonia, 60% methanol and 10% THF. The hubs and ports were dipped as described above.

All of the treated hubs and ports were tested for antimicrobial properties on trypticase soy agar plates seeded with 0.3 ml of *S. aureus* culture ($10^5$ CFU/ml). The hubs and ports were placed on the surface of the agar plate and incubated for 24 hours. The zone of inhibition around the device was then measured, after which the device was transferred to a fresh plate for further incubation. The results in Table J show the benefits of impregnation using the ammonia/methanol/THF solvent system.

This impregnation system may be used for other catheter parts, e.g., extension lines, or for impregnation of the luminal surface of the catheter body prior to exterior coating.

TABLE J

| Procedure | Days | Zone of Inhibition (mm) | | | |
|---|---|---|---|---|---|
| | | 1 | 2 | 3 | 4 |
| 1 | Hub | 10 | 0 | — | — |
| | Port | 15 | 0 | — | — |
| 2 | Hub | 23 | 14 | 13 | 15 |
| | Port | 25 | 16 | 14 | 15 |
| 3 | Hub | 20 | 13 | 13 | 12 |
| | Port | 21 | 17 | 15 | 14 |

EXAMPLE: DUAL COATING CATHETERS

Catheter segments for use in accordance with the invention were prepared by soaking triple lumen polyurethane catheter segments (Arrow International) in a solution containing 20 mg% of teicoplanin, a glycopeptide antibiotic, in 50% ethanol:50% water for two hours at 20°–30° C. After drying at room temperature for 30 minutes they were rinsed in water and dried again. The ends were then sealed by heating, and the sealed segments were dipped in a solution containing 3% polyurethane, 1.5% CHA and 0.75% AgSD in 30% ethanol:70% THF. The dipped segments were dried at 70 degrees Centigrade for 30 minutes and then tested for bacterial adherence in accordance with the procedures set forth above.

The results of this experiment are shown in Table K. As can be seen, the segments treated on both the interior and exterior surfaces showed marked superiority to the control samples.

TABLE K

| Inner Anti-infective | Outer Coating | Bacterial Adherence After Prolonged Soaking in TSB | | |
|---|---|---|---|---|
| | | 0 | 3 days | 4 days |
| Teicoplanin | AgSD + CHA | 0 | 0 | 0 |
| Controls | | | | |
| 0 | AgSD + CHA | 0 | 240 | 270 |
| Teicoplanin | 0 | 100 | 550 | 1,000 |
| 0 | 0 | 100 | >1,000 | >10,000 |

EXAMPLE: DUAL COATING CATHETERS 5 cm catheter segments were coated and impregnated using various combinations of drugs in accordance with the invention. The segments were unsealed and individually soaked in 10 ml volume of TSB at 37° C. in a water bath shaker for 24 hours. A portion of the segments were then placed in a new 10 ml volume of TSB for an additional 24 hours.

The segments, as well as segments which had not been soaked, were then inoculated on the inner luminal surface with *S. epidermidis* ($10^8$ CFU/ml) and placed in petri dishes for 4 hours at 37° C. After 4 hours, the ends of the segments were sealed and the outer surfaces were sterilized with 70% isopropanol. The ends of the segments were then opened, and the lumens were flushed with 1.0 ml of CHA inactivating media (LTSB) three times in succession to remove adherent bacteria. 0.2 ml aliquots of these washings were plated on trypticase soy agar and incubated for 24 hours at 37° C. The colonies were then counted to provide an indication of the level of luminal bacterial adherence after various periods of soaking which would tend to leach out the antiinfective agent. The results are shown in Table L.

As is apparent from these results, the inner luminal coating was resistant to leaching and provided excellent resistance to bacterial growth.

TABLE L

| Inner Anti-infective | Outer Coating | Adherence of *Staph. aureus* (CFU/cm) | | |
|---|---|---|---|---|
| | | 0 | 1 day | 2 day |
| CHA | AgSD + CHA | 0 | 77 | 150 |
| AgSD + CHA | AgSD + CHA | 0 | 35 | 200 |
| HBC | AgSD + CHA | 0 | 0 | 0 |
| Controls | | | | |
| 0 | AgSD + CHA | 1,000 | >5,000 | >5,000 |
| 0 | 0 | >10,000 | >10,000 | >10,000 |

EXAMPLE: ANTIINFECTIVE CATHETER ASSEMBLIES

Catheter segments, hubs and ports were rendered antiinfective by soaking in 0.2% AgSD and 2% CHA in 20% Ammonia/60% Methanol/20% THF (Soaking Solution A); 0.1% AgSD and 2% CHA in 20% Ammonia/60% Methanol/20% THF (Soaking Solution B); 2% CHA and 0.1% benzalkonium chloride in 80% methanol/20% THF (Soaking Solution D) or 3% CHA in 50% methanol/50% THF (Soaking Solution D). The materials were soaked in the above-described solutions, dried for one hour, and then placed on a trypticase soy agar plates and incubated. The zone of inhibition around each soaked piece was measured at the end of 1, 2, 3 and 4 days of incubation. The results of this study are reported in Table M. As is apparent from the results, each of the solutions was able to impart substantial levels of antiinfectivity, that lasted for the full four days of the test.

Various patents and other publications, cited herein, are hereby incorporated by reference in their entirety.

TABLE M

| SOLUTION | HUB | | | | PORT | | | | CATHETER SEGMENT | | | |
| --- | --- | --- | --- | --- | --- | --- | --- | --- | --- | --- | --- | --- |
| DAY | A | B | C | D | A | B | C | D | A | B | C | D |
| 1 | 21 | 21 | 21 | 22 | 22 | 25 | 24 | 25 | 12 | 12 | 18 | 20 |
| 2 | 15 | 12 | 13 | 13 | 18 | 18 | 17 | 17 | 12 | 11 | 13 | 13 |
| 3 | 12 | 12 | 9 | 9 | 16 | 17 | 16 | 17 | 9 | 8 | 12 | 10 |
| 4 | 9 | 8 | 8 | 9 | 13 | 16 | 15 | 15 | 8 | 4 | 10 | 10 |

What is claimed is:

1. An injection port comprising an antiinfective insert selected from the group consisting of an antiinfective disc and an antiinfective ring, wherein the antiinfective disc or antiifective ring is comprised of a ploymer which has been impregnated, at its surface, with an antiifective agent.

2. The injection port of claim 1, in which the antiinfective insert is an antiifective Dacron disc.

3. The injection port of claim 1, in which the antiifective insert in an antiifective polyurethane disc.

4. The injection port of claim 2, in which the antiinfective Dacron disc comprises chlorhexidine or a pharmaceutically acceptable salt thereof.

5. The injection port of claim 3, in which the antiinfective polyurethane disc comprises silver sulfadiazine.

* * * * *

UNITED STATES PATENT AND TRADEMARK OFFICE
CERTIFICATE OF CORRECTION

PATENT NO. : 5,567,495

DATED : October 22, 1996

INVENTOR(S) : Modak et al.

It is certified that error appears in the above-indentified patent and that said Letters Patent is hereby corrected as shown below:

Col. 5, line 9, "Benzalkonium" should read --benzalkonium--;

Col. 5, lines 43-44, "undesireable" should read --undesirable--;

Col. 7, line 33, "undesireable" should read --undesirable--;

Col. 7, line 35, "to me" should read --to be--;

Col. 8, line 49, "benzalkonium chloride" should read --Benzalkonium Chloride--;

Col. 8, line 52, "benzalkonium chloride" should read --Benzalkonium Chloride--;

Col. 9, line 13, "benzalkonium chloride" should read --Benzalkonium Chloride--;

Col. 9, line 16, "benzalkonium chloride" should read --Benzalkonium Chloride--;

Col. 9, line 62, "benzalkonium chloride" should read --Benzalkonium Chloride--;

Col. 21, line 1, "plates" should read --plate--;

Col. 22, line 6, "antiifective" should read --antiinfective--;

UNITED STATES PATENT AND TRADEMARK OFFICE
CERTIFICATE OF CORRECTION

PATENT NO. : 5,567,495    Page 2 of 2
DATED : October 22, 1996
INVENTOR(S) : Modak et al.

It is certified that error appears in the above-indentified patent and that said Letters Patent is hereby corrected as shown below:

Col. 22, line 6, "ploymer" should read --polymer--;

Col. 22, line 7, "antiifective" should read --antiinfective--;

Col. 22, line 9, "antiifective" should read --antiinfective--;

Col. 22, line 10, "antiifective" should read --antiinfective--;

Col. 22, line 11, "in an antiifective" should read --is an antiinfective--;

Signed and Sealed this

Eleventh Day of March, 1997

Attest:

BRUCE LEHMAN

Attesting Officer    Commissioner of Patents and Trademarks